United States Patent [19]

Saito et al.

[11] 4,279,616
[45] Jul. 21, 1981

[54] METHOD FOR MEASURING BLOOD COAGULATION AND DEVICE THEREFOR

[75] Inventors: Yukio Saito; Koichi Sekiya; Masaaki Takahashi; Seigo Akiyama, all of Hiromachi, Japan

[73] Assignee: Sankyo Company Limited, Tokyo, Japan

[21] Appl. No.: 70,797

[22] Filed: Aug. 29, 1979

[30] Foreign Application Priority Data

Aug. 30, 1978 [JP] Japan .............................. 53-106566

[51] Int. Cl.³ ...................... G01N 33/16; G06F 15/42
[52] U.S. Cl. .................................. 23/230 B; 23/918; 23/926; 73/61.4; 356/39; 422/73
[58] Field of Search ................ 23/230 B, 918; 422/73; 364/414, 415, 426, 733; 356/39; 250/565; 73/61.4

[56] References Cited

U.S. PATENT DOCUMENTS

| | | |
|---|---|---|
| 3,458,287 | 7/1969 | Gross et al. ............................. 422/73 |
| 3,658,480 | 4/1972 | Kane et al. ............................. 422/73 |
| 3,754,866 | 8/1973 | Ritchie et al. ......................... 422/73 |
| 3,814,585 | 6/1974 | Bailly ................................. 422/73 X |
| 3,833,864 | 9/1974 | Keiss et al. ......................... 422/73 X |
| 4,047,890 | 9/1977 | Eichelberger et al. ............. 422/73 X |

Primary Examiner—Michael Marcus
Attorney, Agent, or Firm—Frishauf, Holtz, Goodman and Woodward

[57] ABSTRACT

A method and apparatus is disclosed for measuring blood coagulation factor, operating on the principle wherein the clotting time (T) of a sample of blood to which a reagent has been added is measured; and then the measured clotting time (T) is converted into a quantity (A) in accordance with the equation:

$$\log p \, (A + A_o) - \log p \, (A_n + A_o) = B \, (\log Q \, T - \log Q \, T_n)$$
$$A = (A_n + A_o) \, P^{B \log Q \left(\frac{T}{T_n}\right)} - A_o; \text{ or}$$
$$A = (A_n + A_o) \cdot \left(\frac{T}{T_n}\right)^B - A_o$$

where:
  $A_o$ is an activation value amount taken on the assumption that an apparently negative or positive residual amount of coagulation factors, which are the object of measurement, exists in a diluted blood plasma solution prepared to obtain various values of activation, unit and concentration;
  $A_n$ is the normal or standard activation value of normal blood plasma;
  B is a constant used in converting from clotting time (T) into activation value;
  $T_n$ is the clotting time of said normal blood; and
  P and Q are logarithmic bases;

In order to eliminate the influence caused by $A_o$ and minimize the errors deriving from the conversion.

7 Claims, 8 Drawing Figures

METHOD FOR MEASURING BLOOD COAGULATION AND DEVICE THEREFOR

CROSS REFERENCE TO RELATED APPLICATION

U.S. Application Ser. No. 944,783, filed Sept. 22, 1978, now U.S. Pat. No. 4,217,107, assigned to the same assignee as the present application, and the entire contents of which are incorporated herein by reference.

BACKGROUND OF THE INVENTION

The present invention relates to an improvement in measuring devices for blood clotting time.

Measurement of blood clotting time is widely employed to test blood coagulation functions. Typically known methods are Prothrombin Time measurement (PT) for testing the extrinsic coagulation system, Activated Partial Thromboplastine Time measurement (APTT) for the intrinsic system and Partial Thromboplastine Time measurement (PTT). There are also such methods as PT type coagulation time measurement (FAPT) and APTT type coagulation time measurement (FA-APTT) to study various factors of coagulation with the use of a sample which is diluted by a plasma devoid of coagulation factors. TT type coagulation time is also tested to learn the amount of fibrinogen present in the blood (FIBT).

The coagulation function of blood has heretofore been tested by measuring clotting time. Most of the reagents employed in the measurement of blood clotting time are made of organic extracts, and this may lead to an error that the same normal plasma may produce different results in measurement of clotting time when coagulation reagents of more than one production lot are used. Different results may be obtained even if the same normal plasma is measured for its clotting time when the reagents, made for identical purposes, were made of different materials or by different production methods.

The recent trend is that it is considered inappropriate to indicate the coagulation function in terms of clotting time. Instead, there has been an attempt to test the coagulation function by means of a ratio (R) or an activation value (A). In the former, the clotting time of normal plasma (Tn) is measured for every measurement to obtain a ratio value (R) by dividing the clotting time (T) of each sample by said normal plasma clotting time (Tn), that is R=T/Tn, which expresses coagulation function. The latter method employs an activation value, unit or concentration, since such values indicate the coagulation function more directly than the value R.

In the measurement of PT and APTT by the said latter (activation value) method, the normal plasma is first diluted with physiological saline solution (PSS). On the assumption that the plasma concentration of this diluted solution represents the activation value A (%) of the coagulation function, each diluted solution of different normal plasma concentration is measured for its clotting time. The normal plasma therefore has the activation value of 100%.

The relation of clotting time to activation value is plotted on graph, and a curve which coincides with each point of measured values is drawn. The curve is termed as the activation curve, which is used as a calibration curve to determine the activation value A from the clotting time T. It is therefore possible to determine the activation value A from the clotting time T, and it is possible to determine the activation value from the said curve in the graph if the clotting time of a patient's plasma is measured.

The coagulation function thus expressed in activation value from the activation curve instead of in clotting time shows an improvement in correspondency of its values with the coagulation function. Although its reproducibility was insufficient, it has been possible to obtain the activation curve of PT, whereas that of APTT was not obtainable. This is due to the fact that the detection of the clotting end point was not sufficient in the conventional clotting time measuring device. The method disclosed in U.S. Application Ser. No. 944,783, filed Sept. 22, 1978 (corresponding to Japanese Application No. 52-118730) enables the detection of the clotting end point, and the activation curve of APTT as well as that of PT can now be obtained with an excellent reproducibility.

FIG. 1 illustrates an activation curve of APTT which is obtained in accordance with the above method using the technique of U.S. Ser. No. 944,783. It is naturally preferable to measure the activation value A (%) directly by an on-line system. Now that activation curve is obtainable with a high reproducibility as mentioned above, it is possible to use an on-line system instead of conventional hand-plotted graphs.

However, the activation curve is not a mere linear or quadratic function, and therefore non-linear conversion of functions is required in order to indicate the activation value A from measured clotting time by an on-line system. The function which is easily assumed in a non-linear conversion such as this is an equation of higher degree.

$$y = a + bx + cx^2 + dx^3 + ex^4 + fx^5$$

However, it is not easy to determine the constants, a, b, c . . . in the above equation, and furthermore, these constants may vary depending on the production lots of the coagulation reagents.

The object of the present invention is to provide non-linear conversion from clotting time T to activation value Ac.

SUMMARY OF THE INVENTION

A method for measuring blood coagulation factor, comprises measuring the clotting time (T) of a sample of blood to which a reagent has been added; and then converting the measured clotting time (T) into a quantity (A) in accordance with the equation:

$$\log p \,(A + Ao) - \log p \,(An + Ao) = B \,(\log Q \, T - \log Q \, Tn)$$
$$A = (An + Ao) \, P^{B \log Q (\frac{T}{Tn})} - Ao; \text{ or}$$

$$A = (An + Ao) \cdot \left(\frac{T}{Tn}\right)^B - Ao$$

where:

Ao is an activation value amount taken on the assumption that an apparently negative or positive residual amount of coagulation factors, which are the object of measurement, exists in a diluted blood plasma solution prepared to obtain various values of activation, unit and concentration;

An is the normal or standard activation unit and concentration value of normal blood plasma;

B is a constant used in converting from clotting time (T) into activation value;

Tn is the clotting time of said normal blood; and
P and Q are logarithmic bases;
in order to eliminate the influence caused by Ao and minimize the errors deriving from the conversion.

The invention also includes apparatus for measuring the blood coagulation factor in accordance with the above principles, and a method of operating the apparatus.

DETAILED DESCRIPTION

Figure 1:
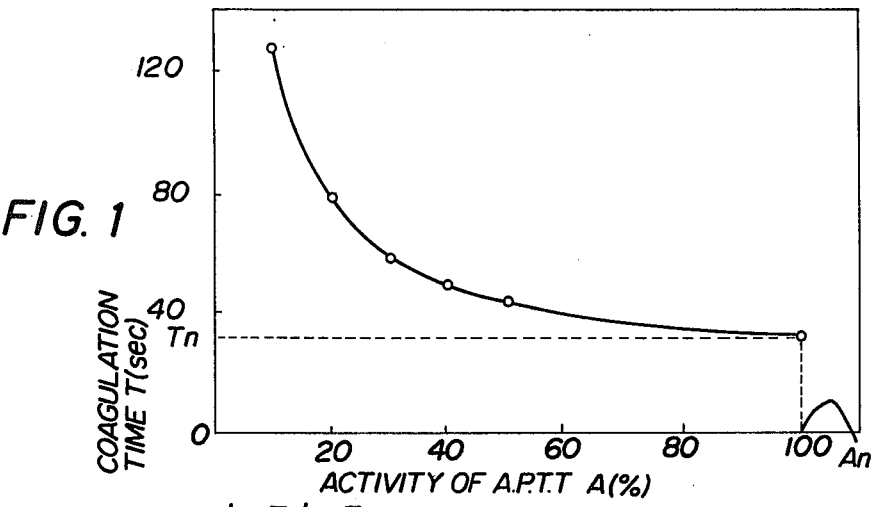
FIG. 1 shows an activation curve illustrating the relation of clotting or coagulation time T (sec) with activation value A (%) in respect of Activated Partial Thromboplastine time (APTT) in blood coagulation measurement.

Conversion of co-ordinates is carried out using the clotting time Tn (sec) at the activation An (%) (normally 100%) of normal plasma with respect to the relation of activation value A (%) with clotting time T (sec) of the APTT activation curve shown in FIG. 1, and the following equation (1) is obtained, assuming that the base of a logarithm P,Q, is 10:

$$\log A - \log An = F(\log T - \log Tn) \qquad (1)$$

where F designates "function of".

Figure 2:
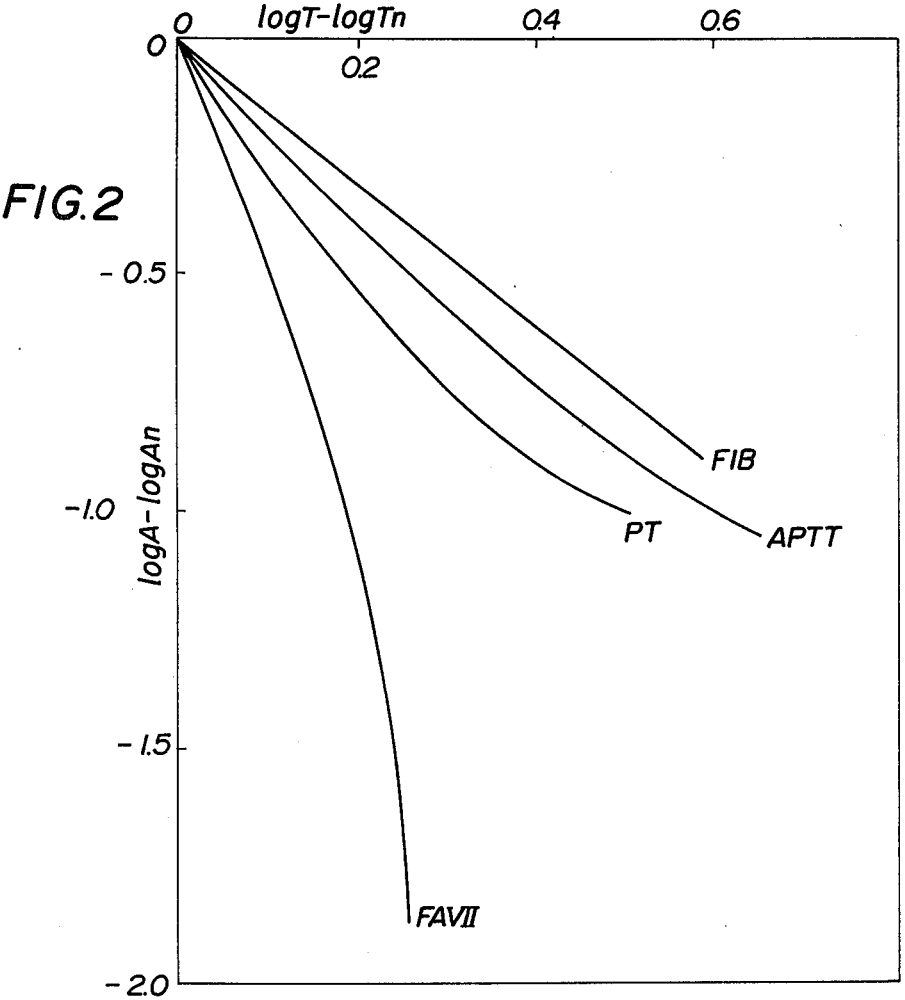
FIG. 2 shows a characteristic curve obtained by converting and plotting the curve in FIG. 1 according to Equation 1 with An and Tn as the standard for conversion.

The measured values in FIG. 1 are converted by the above equation (1) and are plotted to obtain the curve APTT shown in FIG. 2. Likewise, the values of PT, FIB and the factor VII measurement (FAVII) are plotted to obtain the curves indicated at PT, FIB and FAVII in FIG. 2. The measurement of activation with respect to factor VII is conducted as follows. A normal plasma is mixed with Owren's Veronal Buffer to prepare a standard plasma, which is diluted by a plasma devoid of said factor VII. The activation value of the factor VII in the diluted sample is expressed by the concentration of the standard plasma in the sample. The relation of activation value A at this point with clotting time T is expressed by equation (1) and is shown in FIG. 2 as FAVII. The curve FAVII is not linear, as shown in FIG. 2, but the gradient increases toward the negative as the values of abscissa increases.

So far, the discussion has been based on the assumption that plasma devoid of the factor VII contains no factor VII at all. It is now proposed that a small amount of factor VII is present in plasma which is considered to be devoid of the factor VII. Taking this residual amount of factor VII as Ao, Equation (1) is converted into Equation (2):

$$\log (A + Ao) - \log (An + Ao) = F(\log T - \log Tn) \qquad (2)$$

where F designates "function of".

Figure 3:
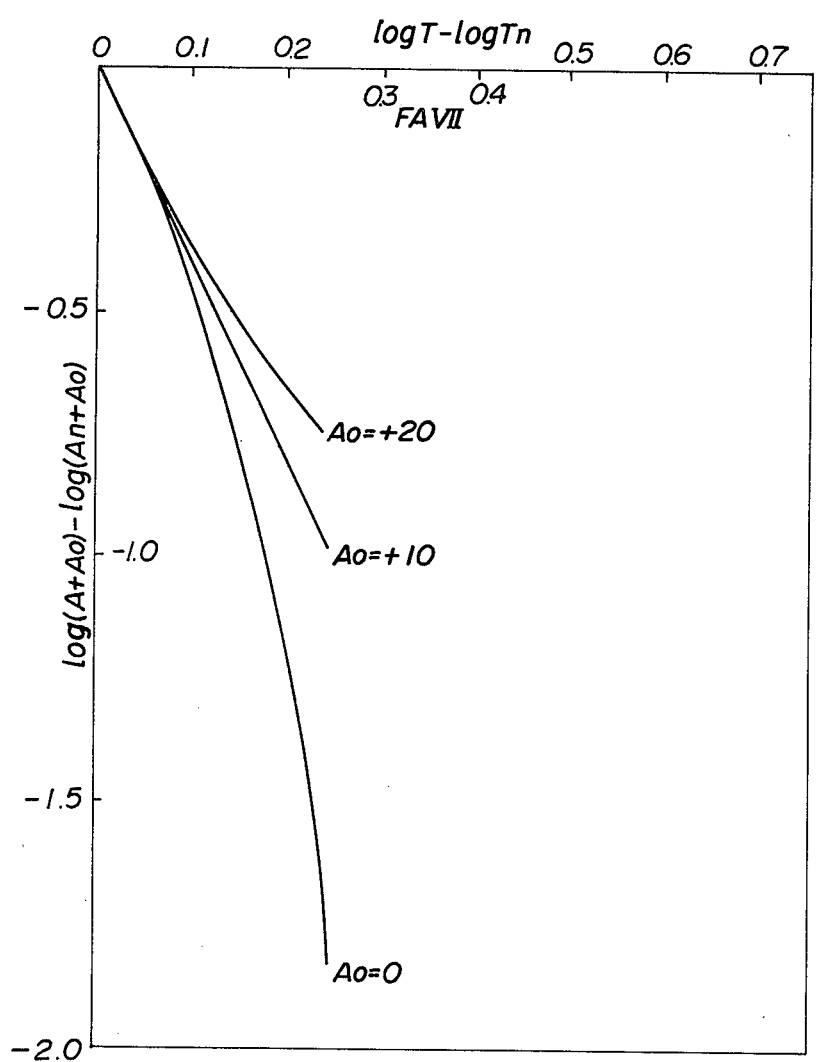
FIG. 3 illustrates a characteristic curve of FAVII obtained by plotting Equation 2 in the same manner as in FIG. 2.

Equation (2) is plotted in the same manner as in FIG. 2 (see FIG. 3). As the value of Ao is increased from 0 to the positive, the proportion of gradient increase toward the negative accompanying the increase in the abscissa becomes smaller, and when the value of Ao coincides with the apparent value of residual factor VII present in the plasma devoid of factor VII, the negative gradient increase accompanying the increase in the abscissa becomes minimum and gradient becomes constant (FIG. 3). At this point, equation (3) is established.

$$\text{Log} (A + Ao) - \log (An + Ao) = B(\log T - \log Tn) \qquad (3)$$

where B designates "gradient".

As the value of Ao further increases, the gradient decreases with the abscissa increase contrary to the above case. As for PT and APTT values, the samples are diluted by PSS as in the foregoing to obtain an overall activation value of the coexisting coagulation factors. Consequently, all the coagulation factors are diluted and, contrary to the case of said factor VII, an apparent negative residue of normal plasma is considered to be present in PSS, the diluent, owing to the interaction between the factors.

Figure 4:
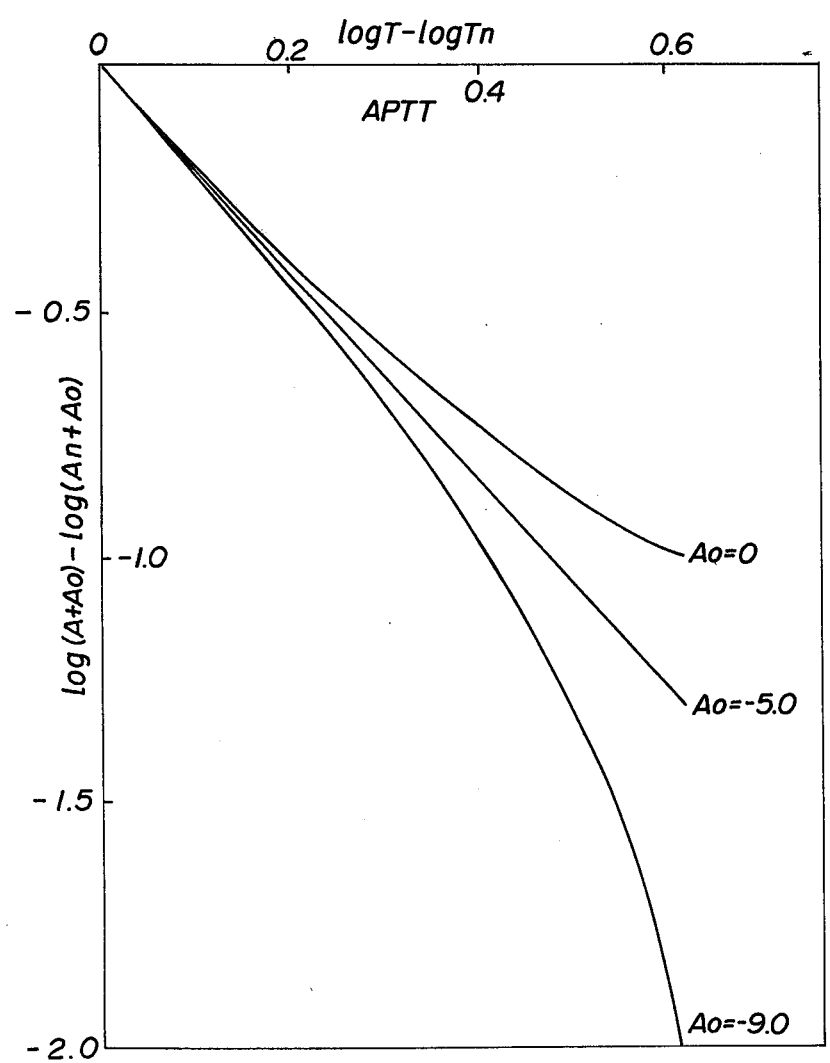
FIG. 4 is a characteristic curve of An and Tn with respect to APTT shown in FIG. 2 according to Equation 2.
Figure 5:
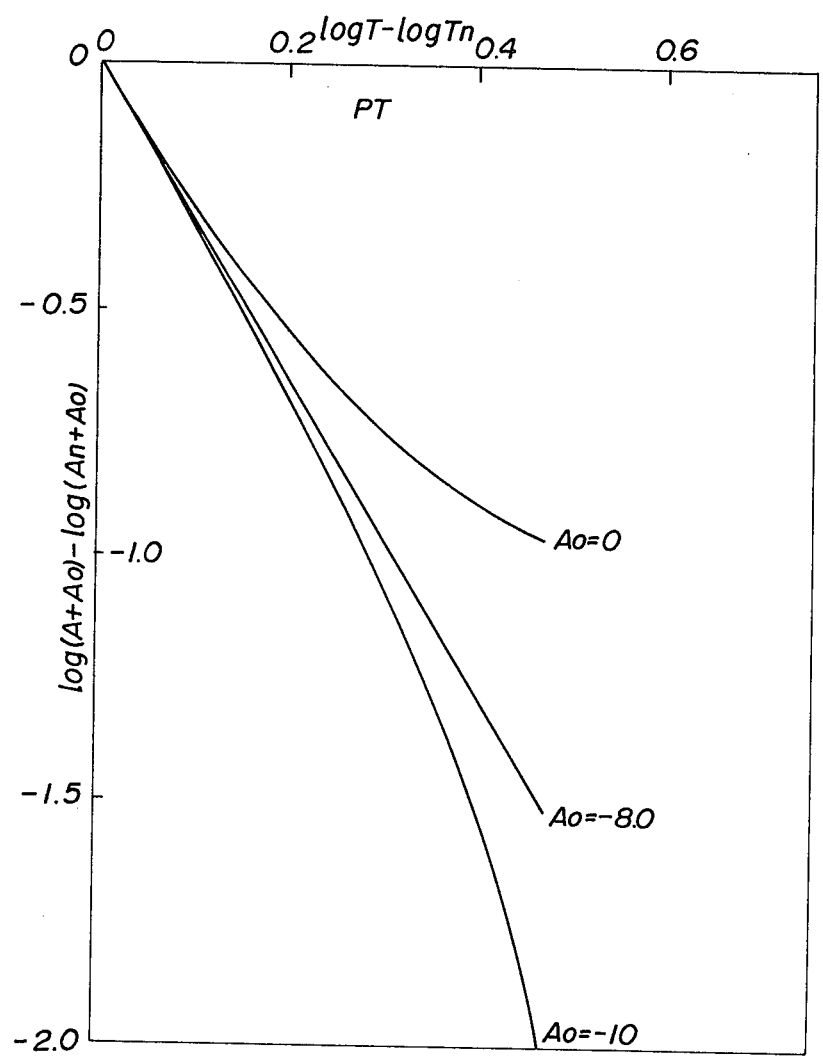
FIG. 5 is a characteristic curve of An and Tn with respect to PT of FIG. 2 according to Equation 2.

Now, when the value of Ao in Equation (2) increases from 0 to the negative, the PT and APTT curves in FIG. 2 show an increase in the gradient corresponding to the increase in the abscissa, and when the values of respective Ao coincide with the apparent negative residues of the normal plasma present in the PSS, the gradient becomes constant (FIGS. 4 and 5). Equation (3) is established at this point. As the value Ao increases still further in the negative, the gradient increases in the negative direction corresponding to the increase in the value of the abscissa.

Equation (3) is established on the assumption that either apparent positive or negative coagulant factors and the like remain in the diluted solution which is prepared to obtain the activation curves with respect to each item in clotting time measurement. Equation (3) is plotted to obtain a graph shown in FIG. 3 and the relation of the ordinate and abscissa is expressed by the constant gradient B in a linear equation.

Thus, by predetermining values of Ao and B from the activation curve, the activation value A can be calculated by the following Equation (4) from the clotting time T of the sample.

$$A = (An + Ao)10^{B \log \left( \frac{T}{Tn} \right)} - Ao \quad \text{or} \qquad (4)$$

$$A = \left\{ (An + Ao) \cdot \left( \frac{T}{Tn} \right)^B \right\} - Ao$$

Ao can be obtained by plotting Equation (3) in the same manner as in FIG. 2 and selecting the values Ao so that the line assumes a linear line. Upon determining said value Ao, the gradient value B is determined by the gradient in the same graph. In this way, the curvature and gradient are corrected by Ao and B respectively.

An electronic circuit in which said Equation (4) is realized is installed in a blood coagulation measuring device. The device first measures the clotting time, and based on the values obtained, said electronic circuit directly indicates and records the activation value, unit or concentration of coagulation functions. When the activation value, unit or concentration is directly indicated by Equation (4), the coagulation functions are indicated more directly than when indicated by clotting time; and moreover, it provides the following merits.

Firstly, as the origin in Equation (4) is defined by the clotting time $T_n$ of either the normal plasma, the standard unit or the concentration, it facilitates correction of $T_n$ as a routine procedure. It is an important aspect of a blood coagulation measuring device that $T_n$ can be corrected easily since in many cases differences deriving from the difference in production lots of coagulation reagent are sufficiently corrected by merely correcting $T_n$ in Equation (4).

Secondly, if the relative equation of clotting time $T$ and activation value $A$ is formed by a higher degree equation, the determination of constants in the equation becomes complicated, involving use of an electronic computer and makes it impossible to intuitively select the constants.

In the present invention, Equation (3) is plotted as shown in FIG. 3, and constant $A_o$ is so selected as to make the plotted line linear by changing the value $A_o$. The gradient of $A_o$ thus defined with respect to abscissa and ordinate in the graph becomes constant, i.e. gradient B. In this way the constants in Equation (4) can be determined by a relatively simple procedure. As for the case of fibrinogen, $A_n$ represents the amount of fibrinogen (mg/dl) contained either in a standard solution of fibrinogen or normal plasma (mg/dl), whose clotting time is $T_n$ and thus $A_c$ is the concentration (mg/dl).

A specific embodiment of apparatus according to the present invention will now be described with reference to FIGS. 6, 7 and 8.

Figure 7:
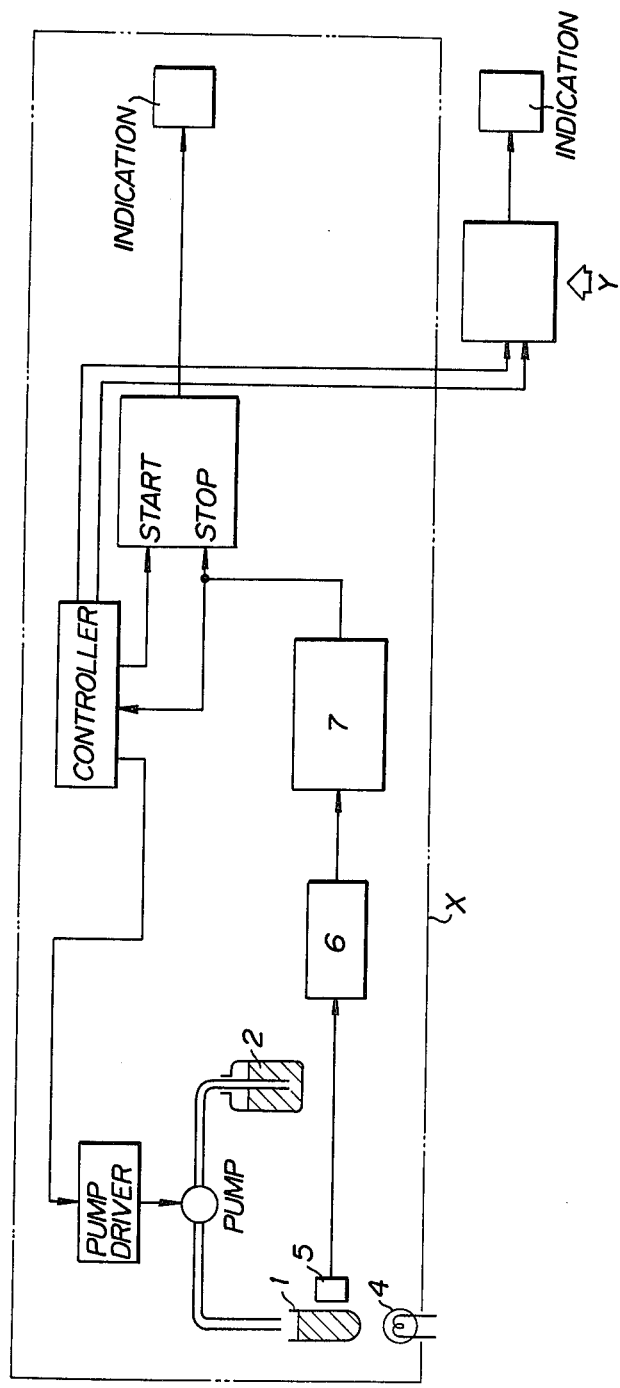
FIG. 7 is an example illustrating the use of the device according to the present invention.
Figure 8:
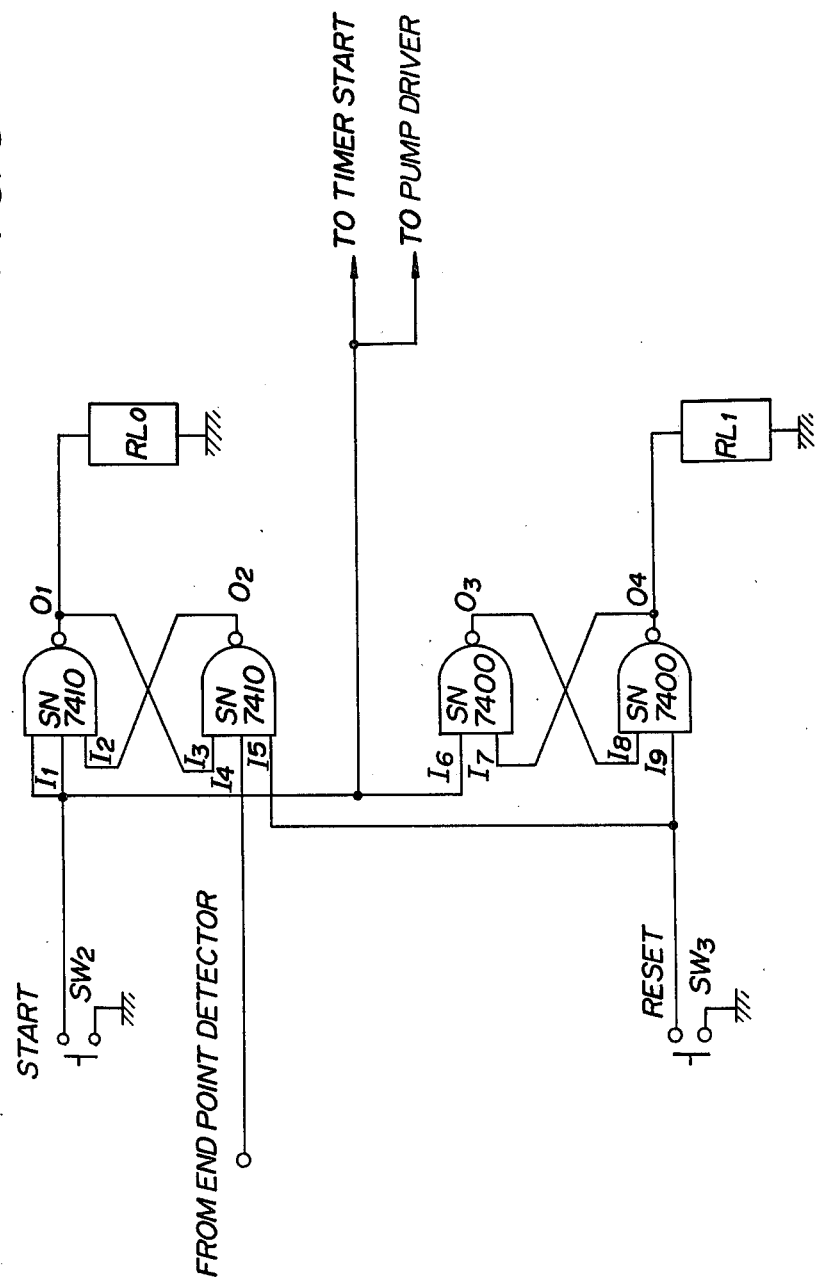
FIG. 8 shows an embodiment of the controller illustrated in FIG. 7.

As shown in FIG. 7 and as well-known in the art, a blood clotting time measuring device performs the measurement in the following way under control of the controller 8: a predetermined quantity of coagulation reagent 2 is added to a plasma solution in a blood coagulation measuring sample chamber 1 by a pump driver 9 driving a pump 10 under control of controller 8, whereupon a timer 3, such as, for example, an electronic timer, is started by controller 8. The light from a light source 4 is directed onto the sample in sample chamber 1 and the light scattered (any other optical density is also applicable) is received by a photoelectric transducer 5 which generates electrical signals corresponding to the optical characteristics of the sample in sample chamber 1. The electrical signals generated by the optical converter 5 are amplified by an amplifier 6 and signals corresponding to the measured light values are introduced into a clotting end point detector 7 which sends out detection signals for indicating the clotting end point to stop said timer 3. Upon stopping of the timer 3, the indicator 11 indicates the stopped timing of the counter which is the coagulation time. Up to this point, the above-described apparatus and method are substantially as described in copending application Ser. No. 944,783, and the detection of the clotting end point is the same as in Ser. No. 944,783.

Figure 6:
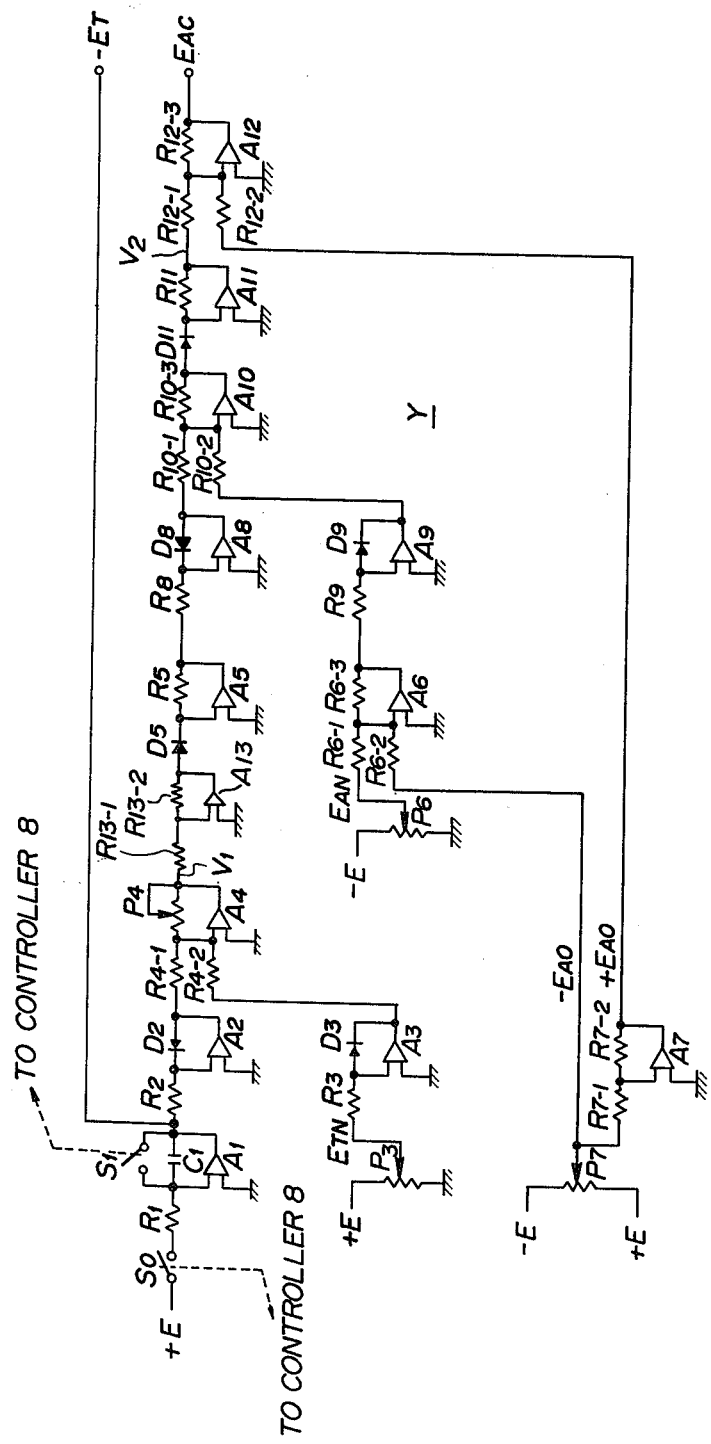
FIG. 6 shows a circuit diagram of a device of the present invention for use in practically applying the method of the present invention.

Switches $S_0$ and $S_1$ shown in FIG. 6 are operated by a controller shown in FIG. 7. FIG. 8 shows an embodiment of the said controller.

When a start switch $SW_2$ of the controller is closed, the input $I_1$ of SN7410 and the input $I_6$ of SN7400 become LOW while their outputs $O_1$ and $O_3$ become HIGH. When the output $O_3$ of SN7400 becomes HIGH, the output $O_4$ of SN7400 becomes LOW. The output $O_1$ of SN7410 turns a relay $RL_0$ ON and closes the switch $S_0$ shown in FIG. 6. The output $O_4$ of SN7400 opens the switch $S_1$ of FIG. 6 to cause the integrator comprising the amplifier $A_1$, the resistance $R_1$ and the capacitor $C_1$ to operate and generate voltage ET in proportion to the time counting from then on.

LOW signal obtained by closing the start switch $SW_2$ is applied to the start of the timer and the drive circuit of the reagent pump, which pump acts to pour the coagulation reagent into plasma and the timer begins to measure the blood clotting time.

When the clotting end point detection signal from the clotting end point detector 7 is applied as a LOW signal to the input $I_4$ of SN7410, its output $O_2$ becomes HIGH while the output $O_1$ of SN7410 becomes LOW to turn the relay $RL_0$ OFF and to open the switch $S_0$ in FIG. 6. When the reset switch $SW_3$ is closed, the input $I_9$ of SN7400 becomes LOW, its output $O_4$ HIGH, the relay $RL_1$ turned ON and the switch $S_1$ of FIG. 6 is turned ON.

After closing the start switch $SW_2$ and before the clotting end point detection signal appears, the reset switch $SW_3$ is closed to cause the input $I_5$ of SN7410 to become LOW, its output $O_2$ HIGH, the relay $RL_0$ OFF and the switch $S_0$ in FIG. 6 becomes open. At this time, the output $O_4$ of SN7400 becomes HIGH so that the relay $RL_1$ becomes ON and the switch $S_1$ of FIG. 6 is closed. Thus, the integrator becomes ready for resetting.

FIG. 6 illustrates an embodiment of a device for carrying out the method of the present invention as applied to a blood clotting time measuring device.

In FIG. 6, the symbols denote operational amplifiers; D denotes log-diodes (i.e., a diode having a logarithmic transfer function); R denotes resistances; C denotes capacitors; S denotes switches; P denotes potentiometers for determining constants; +E is a positive voltage source of, for examle, +10 V; and —E is a negative voltage source of, for example, —10 V.

FIG. 6 shows an embodiment in which Equation (4) is realized by means of an electronic circuit. Switch $S_0$ is initially open and switch $S_1$ is initially closed. With switches $S_1$ and $S_0$ so set, the circuit is in the state of reset. Electrical signals generated by the controllers 8 at the time when coagulation reagent is added to the plasma sample in sample chamber 1 open the switch $S_1$ and close the switch $S_0$, and an integrator comprising amplifier $A_1$, resistance $R_1$ and capacitor $C_1$ is thereby actuated, generating a voltage ET proportional to the passage of time thereafter. This means that this portion of the circuit functions as a timer, and the output voltage ET represents the length of time elapsed from the time of introduction of coagulation reagent to the sample in sample chamber 1.

The switch $S_0$ is opened by means of an electric signal from controller 8 which is worked by an output signal from the clotting end point detector when the plasma sample coagulates. This effectively stops the integrator $A_1$, $R_1$, $C_1$ and the output voltage thereof which corresponds to the time of the clotting end point is retained. Consequently, the voltage ET corresponds to the clotting time T.

Potentiometer $P_3$ generates voltage $ET_n$ in reverse polarity to that of voltage ET, the voltage $ET_n$ corresponding to $T_n$ in Equation (4).

The voltage ET is converted into a logarithmic value by means of a logarithmic converter comprising operational amplifier $A_2$, log-diode $D_2$ and resistance $R_2$. Voltage ETn is likewise converted to logarithmic value by means of logarithmic converter $A_3$, $D_3$ and $R_3$. These logarithmic values are introduced to an adder of variable gain comprising an operational amplifier $A_4$, resistances $R_{4-1}$, $R_{4-2}$ and a potentiometer $P_4$. Since log ET and log ETn are of opposite polarity in this case, the addition results in subtraction.

Potentiometer $P_4$ changes the gain of addition, which functions as a means to determine constant B in Equation (4). However, the constant B is practically negative and $V_1$ is inverted in its polarity by an inverting amplifier comprising an operational amplifier $A_{13}$ and resistances $R_{13-1}$ and $R_{13-2}$. The output obtained through inversion of $V_1$ by said inverting amplifier is therefore a voltage which corresponds to the exponent of Equation (4), and is inversely converted by means of an antilogarithmic converter circuit comprising an operational amplifier $A_5$, a diode $D_5$, and a resistance $R_5$.

A potentiometer $P_6$ generates voltage EAn which corresponds to the constant An in Equation (4). A potentiometer $P_7$ generates voltage EAo which corresponds to the constant $A_0$.

The voltages EAn and EAo are added by an adder comprising an operational amplifier $A_6$ and resistances $R_{6-1}$, $R_{6-2}$ and $R_{6-3}$ to generate a voltage corresponding to An+Ao in Equation (4). The output voltages of operational amplifiers $A_5$ and $A_6$ are multiplied by a multiplier comprising operational amplifiers $A_{8-11}$. That is, the output of the operational amplifier $A_5$ is converted into a logarithm by means of a logarithmic converter comprising an operational amplifier $A_8$, a log-diode $D_8$ and a resistance $R_8$, while the output of amplifier $A_6$ is likewise converted into a logarithmic output by means of $A_9$, $D_9$ and $R_9$.

These outputs are added in an adder comprising an operatinal amplifier $A_{10}$ and resistances $R_{10-1}$, $R_{10-2}$ and $R_{10-3}$, and the sum of these inputs is produced as an output. The output is then fed to the input of an antilogarithmic converter comprising an operational amplifier $A_{11}$, a log-diode $D_{11}$, and a resistance $R_{11}$ to produce an output voltage $V_2$ converted into an antilogarithm.

Specifically, a voltage corresponding to the product of the output voltage from operational amplifiers $A_5$ an $A_6$ is thereby obtained. The polarity of the voltage $-EAo$, on the other hand, is inverted by an inverting amplifier comprising an amplifier $A_7$ and resistances $R_{7-1}$ and $R_{7-2}$.

The outputs of operational amplifiers $A_{11}$ and $A_7$ are added in reverse polarity in an adder comprising an operational amplifier $A_{12}$ and resistance $R_{12-1}$, $R_{12-2}$ and $R_{12-3}$, and the difference output is generated as a voltage EAc which corresponds to the value Ac in Equation (4).

A voltage proportional to the activation value, unit or concentration which corresponds to Equation (4) can therefore be directly obtained from the clotting time by means of the circuit shown in FIG. 6. The method of the present invention enables direct indication and recording of the activation value, unit or concentration of PT, APTT, fiblinogen, II factor, V factor, VII factor, VIII factor, IX factor, X factor, XI factor and XII factor in testing of the coagulation function.

The method of the present invention can be equally well carried by a combination of analog and digital circuits. Equations (1), (2), (3) and (4) are expressed in common logarithm and its inverse conversion with the bases P and Q of 10. It will be the same with a natural logarithm with the base $Q=e$ and its inverse conversion with the base $P=e$. A combination of common logarithms and natural logarithms may also be employed, and the value of logarithm bases P and Q may also be arbitrary.

The switches $S_1$ and $S_0$ shown in FIG. 6 may be solenoid or relay-type switches controlled by appropriate electrical signals coupled thereto, or may be semiconductor switches, as should be apparent.

We claim:

1. A method of measuring blood coagulation factor, comprising:

feeding a voltage ET proportional to coagulation time T of a sample plasma to a dividend input terminal of an analog divider;

feeding a voltage ETn corresponding to normal plasma coagulation time to a divisor input terminal of said analog divider;

feeding the output of said analog divider to an analog log converter;

feeding the output of said log converter to a bipolar analog coefficient circuit in which the coefficient is B;

feeding the output of said coefficient circuit to an input of an analog antilog circuit;

adding a voltage EAn corresponding to activity or concentration of normal plasma to one input terminal of an analog adder;

adding a voltage EAo corresponding to residual activity or residual concentration of coagulation factor defect plasma or diluted solution to another input terminal of said analog adder;

feeding the outputs of said antilog circuit and adder to an input of an analog multiplier; and feeding the output of said adder to a minuend input terminal of an analog subtractor, while feeding said voltage EAo corresponding to said residual activity or residual concentration to a subtrahend input terminal of said analog subtractor;

the output EA of said subtractor being a value proportional to the activity or concentration corresponding to the sample plasma coagulation time T.

2. The method of claim 1, further comprising:

adding a predetermined quantity of coagulation reagent to a plasma solution under the control of a controller;

starting a timing means when said coagulation reagent is added to said plasma solution;

detecting the optical characteristics of the plasma solution to which said predetermined quantity of coagulation reagent has been added;

detecting the clotting end point as a function of said optical characteristics;

stopping said timing means upon detection of said clotting end point, the elapsed time of operation of said timing means being the clotting time T of the sample of blood to which said coagulation reagent has been added; and generating said voltage ET proportional to said elapsed clotting time T.

3. The method of claim 2 wherein said step of generating said electrical signal (ET) corresponding to the measured clotting time (T), comprises integrating a predetermined voltage value over a period of time corresponding to the clotting time of a sample of blood to which a reagent has been added, the result of said integration corresponding to said first-mentioned electrical signal (ET).

4. Apparatus for measuring blood coagulation factor, comprising:

means for measuring the clotting time (T) of a sample of blood to which a reagent has been added, said measuring means including means for receiving a predetermined quantity of coagulation reagent and a plasma solution, a controller for operating said receiving means, timing means connected to the controller for starting a timing operation when the coagulation reagent is added to the plasma solution, means for detecting the optical characteristics of the plasma solution to which the coagulation reagent has been added, means for detecting the clotting end point as a function of the optical characteristics, and means for stopping the timing means upon detection of the clotting end point, the elapsed time of operation of the timing means being the clotting time of the sample of blood to which the coagulation reagent has been added;

first signal generating means coupled to said measuring means for generating a first electrical signal (ET) corresponding to the measured clotting time (T);

second signal generating means for generating a second electrical signal (ETn) corresponding to the clotting time of normal blood;

third signal generating means for generating a third electrical signal (EAo) which corresponds to a constant value which is determined on the assumption that an apparently negative or positive residual amount of coagulation factors, which are the object of the measurement, exists in a diluted blood plasma solution prepared to obtain various values of activation, unit and concentration;

fourth signal generating means for generating a fourth electrical signal (EAn) which corresponds to a constant which is a function of the standard or normal activation value of normal blood plasma;

separate logarithm circuit means coupled to said first and second signal generating means for generating the logarithms of said first and second electrical signals;

first variable gain type adding means coupled to said logarithm circuit means for adding said generated logarithms to generate a fifth electrical signal ($V_1$) which is a function of the sum of said logarithms, said first variable gain type adding means including means for changing the gain of the addition of said generated logarithms;

antilogarithm circuit means coupled to said adding means for generating the antilog of said fifth electrical signal ($V_1$);

second adding means coupled to said third and fourth signal generating means for adding said third and fourth electrical signals;

multiplying means coupled to said first and second adding means, said multiplying means comprising separate logarithmic converter means for logarithmically converting said fifth signal and a signal generated by said second adding means, and third adding means for adding electric signals from said separate logarithmic converter means to produce a sixth electrical signal ($V_2$); and;

fourth adding means coupled to said multiplying means and to said third signal generating means for adding said sixth electrical signal with said third electrical signal to thereby produce an electrical signal which is proportional to the activation unit and concentration value (A) which is a function of the coagulation factor of the blood being measured.

5. Apparatus according to claim 4, wherein said electrical signals are all electrical voltages.

6. Apparatus according to claim 4, wherein said first signal generating means comprises integrating means for integrating a predetermined voltage value over a period of time corresponding to the clotting time of a sample of blood to which a reagent has been added, the result of said integration corresponding to said first electrical signal (ET).

7. The method of claim 4, wherein said second, third and fourth signal generating means comprise respective potentiometers for generating respective voltages corresponding to said respective electrical signals.

* * * * *